United States Patent [19]

Jacobson et al.

[11] Patent Number: 4,593,013

[45] Date of Patent: Jun. 3, 1986

[54] LAYERED COMPOUNDS OF PEROVSKITE RELATED OXIDES AND ORGANIC BASES

[75] Inventors: Allan J. Jacobson, Princeton; Jack W. Johnson, Clinton; Joseph T. Lewandowski, Whitehouse Station, all of N.J.

[73] Assignee: Exxon Research and Engineering Co., Florham Park, N.J.

[21] Appl. No.: 716,040

[22] Filed: Mar. 26, 1985

[51] Int. Cl.$^4$ .............................................. B01J 31/02
[52] U.S. Cl. ..................................... 502/167; 502/401; 502/525
[58] Field of Search .......................... 502/167, 525, 401

[56] References Cited

U.S. PATENT DOCUMENTS

| | | | |
|---|---|---|---|
| 3,905,918 | 9/1975 | Mai et al. | 502/525 X |
| 4,049,583 | 9/1977 | Lauder | 502/525 X |
| 4,126,580 | 11/1978 | Lauder | 502/525 X |

FOREIGN PATENT DOCUMENTS 2155338  5/1973  Fed. Rep. of Germany ...... 502/525

*Primary Examiner*—Patrick P. Garvin
*Attorney, Agent, or Firm*—Henry E. Naylor

[57] ABSTRACT

Disclosed are a class of compositions, and methods of preparing them, which compositions are comprised of inorganic oxides and organic bases. The compositions have layered structures and are represented by the formula $$Z_a H_b M_c [A_{n-1} B_n O_{3n+1}]$$

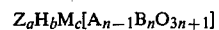

where Z is an organic base having a conjugate acid with a pKa value greater than about 3, H is hydrogen, M is a monovalent cation, $0 < a \leq 2$, $c < 1$, and $b + c = 1$; A is a mono-, di-, or trivalent cation, B is a transition metal, n is an integer from 3 to 7.

16 Claims, No Drawings

LAYERED COMPOUNDS OF PEROVSKITE RELATED OXIDES AND ORGANIC BASES

FIELD OF THE INVENTION

The present invention relates to a class of compositions comprised of inorganic oxides and organic bases. The compositions have layered structures and are represented by the formula $$Z_a H_b M_c [A_{n-1} B_n O_{3n+1}]$$

where Z is an organic base having a conjugate acid with a pKa value greater than about 3, H is hydrogen, M is a monovalent cation, $0 < a \leq 2$, $c < 1$, and $b+c=1$; A is a mono-, di-, or trivalent cation, B is a transition metal, n is an integer from 3 to 7.

BACKGROUND OF THE INVENTION

Perovskite-type structures are formed by $ABX_3$-type compounds where A atoms replace some of the X atoms in close-packed cubic layers and the B atoms fit in the sites octahedrally coordinated X atoms. Because of the flexibility of the perovskite structure with regard to substitution of a wide range of cations as well as modification of the structure itself, perovskites have proved useful for many applications. For example, U.S. Pat. No. 4,482,644 to Beyerlein et al. teaches oxygen-deficient barium-containing perovskites for use in oxidative dehydrogenation reactions.

Also, the perovskite structure has been modified to produce a two-dimensional structure in which additional cations separate perovskite-like layers. Such materials include $Bi_2MoO_6$, which has been used in oxidation catalysis. See "Chemistry of Catalytic Processes", by B. C. Gates, J. R. Katzer and G. C. A. Schuit, McGraw-Hill, 1979, Chapter 4.

Furthermore, a series of perovskite-type compositions, represented by the formula $M[Ca_2Nb_3O_{10}]$ where M is Li, Na, K, Rb, or Cs, have been synthesized. See M. Dion, M. Ganne and M. Tournoux, Mat. Res. Bull. 16, 1429, 1981. These compositions are layered inorganic oxide structures wherein each layer is three Nb-oxygen octahedra thick. Such compositions are an example of a general type of structure which may be written $M[A_{n-1}B_nO_{3n+1}]$ where the contents of the parenthesis are the perovskite-like layer and M is the charge balancing interlayer cation.

Compositions represented by the above formula where M is one or more of K, Rb, Cs, NH4, Tl, Ag, and hydrogen; A is one or more mono-, di-, or trivalent cations selected from the group consisting of Groups 1a, 2a, and 3b and the lanthanides, B is one or more transition metals selected from Re, and Groups 4b, 5b, and 6b of the Periodic Table of the Elements and n is an integer from 3 to 7, with the proviso that when n is equal to 3, and M is not hydrogen, B cannot be Nb, are described in a co-pending application U.S. Ser. No. 716,039, filed Mar. 26, 1985, and incorporated herein by reference.

Although perovskite-type compositions have been developed for various uses, there still exists a need in the art for the development of additional perovskite-type compositions.

SUMMARY OF THE INVENTION

In accordance with the present invention, there are provided compositions comprised of layered inorganic oxides and organic bases, which compositions are represented by the formula:

$$Z_a H_b M_c [A_{n-1} B_n O_{3n+1}]$$

where Z is one or more organic bases having conjugate acids with a pKa value greater than about 3, H is hydrogen, M is one or more of K, Rb, Cs, NH4, Li, Na, Tl and Ag; $0 < a \leq 2$, $c < 1$, and $b+c=1$; A is one or more mono-, di-, and trivalent cations selected from Groups 1a, 2a, and 3a of the Periodic Table of the Elements and the lanthanides; B is one or more transition metals selected from Re, and Groups 4b, 5b, and 6b of the Periodic Table of the Elements; and n is an integer from 3 to 7.

In preferred embodiments of the present invention, Z is one or more substituted amines represented by $NR_3$, $NHR_2$, or $NH_2R$ where each R is independently a $C_1$–$C_{36}$ aliphatic, $C_3$–$C_8$ cycloaliphatic, a $C_7$–$C_{24}$ aralkyl, or $C_6$–$C_{10}$ aryl group.

In other preferred embodiments of the present invention no M cation is present, that is, $c=0$.

In still other preferred embodiments of the present invention, there is provided a method for the preparation of the compositions of the present invention. The method comprises: (a) treating a layered inorganic oxide material represented by the formula $M[A_{n-1}B_nO_{3n+1}]$ where M, A, B, and n are as previously defined, with a mineral acid such as hydrochloric acid, nitric acid, and sulfuric acid, to form the corresponding solid acid; and (b) reacting the solid acid with organic bases having conjugate acids with pKa values greater than about 3, at an effective temperature and for an effective amount of time.

DETAILED DESCRIPTION OF THE INVENTION

Compositions which are the subject of the present invention are those compositions represented by the formula:

$$Z_a H_b M_c [A_{n-1} B_n O_{3n+1}]$$

where Z is one or more organic bases having conjugate acids with pKa values greater than about 3, H is hydrogen, M is one or more of K, Rb, Cs, NH4, Li, Na, Tl, and Ag; $0 < a \leq 2$, $c < 1$, and $b+c=1$; A is one or more of mono-, di-, and trivalent cations selected from Groups 1a, 2a, and 3b of the Periodic Table of the Elements and the lanthanides; B is one or more transition metals selected from Re, and Groups 4b, 5b, and 6a of the Periodic Table of the Elements, and n is an integer from 3 to 7. The Periodic Table referred to throughout this specification is found on the inside cover of the Handbook of Chemistry and Physics, 55th Edition, CRC Press, 1974–1975.

Nonlimiting examples of organic bases having conjugate acids with pKa values greater than about 3 which may be used in the practice of the present invention are those set forth below.

Substituted amines represented by $NR_3$, $NHR_2$, and $NH_2R$, where each R can independently be selected from the group consisting of $C_1$–$C_{36}$ aliphatic, $C_3$–$C_8$ cycloaliphatic, $C_7$–$C_{24}$ aralkyl and $C_6$–$C_{10}$ aryl.

When R is aliphatic having from about 8–36 carbon atoms, it may be interrupted by one or more ester, ether, or amido linkages. Nonlimiting examples of such compositions include the polyether amines sold under the tradename JEFFAMINE by Texaco Chemical Co. Specific nonlimiting examples of such polyether amines include

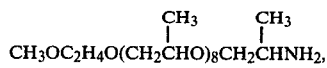

and

Diamines and triamines with similar substituents are also suitable bases. Nonlimiting examples include ethylene diamine, diethylene triamine, hexamethylene, diamine, 4,4'-bipyridine, and 1,4-diaminobenzene.

Also included are heterocyclic compounds wherein the heteroatom is nitrogen. Nonlimiting examples of such compounds include pyridine and substituted pyridines, such as 2-ethylpyridine, 2,4-dimethylpyridine, 4-methylpyridine, and bipyridine. Other organic bases suitable for use herein are piperidine and substituted piperidines, such as 1-n-butylpiperidine and 1,2-dimethylpiperidine.

Multi-ring nitrogen heterocyclic compounds are also suitable for use as the organic base. Such compounds include phenanthroline, guinoline, and isoquinoline.

Preferred are the $C_1$-$C_{36}$ aliphatic amines and the polyether amines.

The compositions of the present invention may be prepared from a solid acid represented by the formula:

$$H_bM_c[A_{n-1}B_nO_{3n+1}]$$

where H is hydrogen, M is a monovalent cation as previously defined, $c<1$, and $b+c=1$; and A, B, and n are as previously defined. The solid acid is reacted with one or more organic bases with a conjugate acid having a pKa of at least about 3, at an effective temperature and for an effective amount of time. The term effective temperature means a temperature high enough to cause the reagents to react, but not so high as to cause decompositon of the organic base material. Generally, this temperature will range from about 20° C. to about 200° C., preferably from about 40° C. to about 100° C. The term effective amount of time means at least that amount of time required to achieve a predetermined completion of reaction. This time will generally range from about 4 to about 600 hours.

It is preferred to have the organic base in liquid form during the reaction of the present invention. Consequently, if the organic base is normally in solid form, or in the form of a viscous liquid, at reaction temperature, then it is preferred to first dissolve the base in any appropriate solvent. Nonlimiting examples of solvents suitable for use in the practice of the present invention include water, $C_5$-$C_{10}$ paraffins, and toluene. After the reaction is complete, the remaining solids can be separated from the liquids by any suitable physical separation technique, such as, filtration or centrifugation.

The solid acid used in the above reaction can be prepared from a layered inorganic oxide material represented by the formula $M[A_{n-1}B_nO_{3n+1}]$, where M, A, B, and n are as previously defined. The solid acid is produced by treating the oxide material with a mineral acid, such as hydrochloric acid, nitric acid, and sulfuric acid, at a temperature from about 20° C. to about 150° C., preferably about 40° C. to about 80° C., for a time from about 1 to 24 hours, preferably from about 1 to 16 hours.

The amount of organic base employed relative to the amount of solid acid is not critical as long as enough base is used to achieve a predetermined level of reaction of base with the solid acid at a reasonable rate. The ratio of organic base to solid acid will typically be from about 0.1 to about 100, preferably from about 0.1 to about 3.

The compositions of the present invention are layered structures comprised of complex layers wherein the complex layers are separated by an interlayer region comprised of Z and H and optionally M, as defined above. The complex layers are comprised of cations of A and B, as previously defined, which are bonded to oxygen atoms in an arrangement similar to that found in typical perovskite structures, except the materials of the present invention are two-dimensional structures as opposed to three-dimensional structures. More specifically, the structure of the complex layers of the materials of the present invention is similar to that observed in $K_2NiF_4$ related structures. See *Structure and Properties of Inorganic Solids*, by F. S. Galasso, Pergamon Predd 1970, Chapter 7. Each of these complex layers contains n sublayers comprised of B cations octahedrally coordinated by the oxygen atoms. Consequently, as n increases, the number of $BO_6$ octahedra sublayers increases proportionately resulting in a complex layer structure of increased thickness.

The compositions of the present invention differ from the $K_2NiF_4$ related structures both in the composition and thickness of the complex layers and the composition of the interlayer.

The compositions of the present invention may be characterized by any appropriate analytical technique. For example the extent of the reaction of organic base with solid acid can be determined by thermogravimetric oxidation of the organic base. Powder x-ray diffraction can be used to determine the increase in the thickness of the interlayer region which increase correlates with the incorporation of the specific organic base. The identification of the particular cations can be determined by conventional elemental analysis techniques.

The materials of the present invention have two dimensionally bonded layer structures with organic molecules in the interlayer region. They are useful as solid sorbents for organic liquids and gases.

The present invention may be further understood by reference to the following examples, which are not intended to restrict the scope of the claims appended hereto.

EXAMPLES 1–18

Compounds of the general composition $(H(CH_2)_mNH_2)_xHCa_2Nb_3O_{10}$ were prepared by reaction of the primary amine, $H(CH_2)_mNH_2$ where $1 \leq m \leq 18$ with $HCa_2Nb_3O_{10}$. The starting compound $HCa_2Nb_3O_{10}$ was prepared by heating $KCa_2Nb_3O_{10}$ at 60° C. for 18 h in 6M HCl. $KCa_2Nb_3O_{10}$ was prepared by reaction in air of stoichiometric amounts of $Ca_2Nb_2O_7$, $Nb_2O_5$ and $K_2SO_4$; first at 750° C. for 18 h and then at 1250° C. with three intermediate regrinds for a total of 120 h. Reactions with methylamine (m=1) and ethylamine (m=2) were carried out in aqueous solution at 50° C. and 25° C. respectively. For propylamine (m=3), the reaction was carried out in a refluxing suspension of $HCa_2Nb_3O_{10}$ in the pure amine (BPt 48° C.). All of the other reactions were carried out in refluxing heptane (BPt 98° C.) solutions of the pure amine in which solid $HCa_2Nb_3O_{10}$ was suspended. As the chain length (m) increased, longer reaction times were necessary. The reaction times are given in Table I. After reaction, the suspensions were cooled and the solid products recovered by filtration. The products were washed with heptane and ethanol and dried at room temperature. The extent of reaction (x) was determined by thermogravimetric oxidation of the organic group and the phase purity by X-ray diffraction. X-ray diffraction patterns of the compounds with $1 \leq m \leq 11$ were single phase with the tetragonal cell constants given in Table I. The c axes spacings, indicative of the interlayer thickness, show a progressive increase as the hydrocarbon chain length m increases. However, for compounds with $12 \leq m \leq 16$, two phases are observed by X-ray diffraction, both of which have expanded interlayer spacing relative to the hydrogen containing starting compound. One of the two phases in each case has the interlayer separation which would be extrapolated from the data for the compounds with $m \leq 11$. Single phase materials with interlayer separations lying on this extrapolated line can be prepared by heating the two phase materials at about 100° C. followed by quenching to room temperature. The second of the two phases has a larger interlayer separation which also increases linearly as n increases. Compounds prepared with amines with m=17 and 18 show the presence of only this phase.

TABLE I $(H(CH_2)_mNH_2)_xHCa_2Nb_3O_{10}$ Compounds

| m | Synthesis time (h) | x | c (Å) | c (Å) |
|---|---|---|---|---|
| 1 | 113 | 0.92 | 16.12 | — |
| 2 | 308 | 1.13 | 20.55 | — |
| 3 | 140 | 1.05 | 22.28 | — |
| 4 | 144 | 1.09 | 24.95 | — |
| 5 | 144 | 1.01 | 26.72 | — |
| 6 | 144 | 1.01 | 28.32 | — |
| 7 | 144 | 1.03 | 30.16 | — |
| 8 | 322 | 1.04 | 31.51 | — |
| 9 | 203 | 0.9 | 33.24 | — |
| 10 | 231 | 0.95 | 34.58 | — |
| 11 | 203 | 0.97 | 36.50 | — |
| 12 | 65 | 0.97 | 37.95 | 44.10 |
| 13 | 203 | 0.95 | 39.85 | 46.35 |
| 14 | 225 | 0.99 | 41.40 | 48.45 |
| 15 | 161 | 1.00 | 43.26 | 51.22 |
| 16 | 64 | 1.01 | 44.90 | 52.82 |
| 17 | 548 | 1.20 | — | 55.59 |
| 18 | 88 | 1.06 | — | 57.47 |

EXAMPLE 19

A sample of $HCa_2Nb_3O_{10}$ (1 g) was heated with excess pyridine under refluxing conditions for 135 h. The product was filtered, washed with ethanol and dried at room temperature. The product was single phase by X-ray diffraction with lattice parameters of a=3.856 Å and c=18.55 Å. Thermogravimetric oxidation gave a composition of $(C_6H_5N)_{0.56}HCa_2Nb_3O_{10}$. A similar experiment in which pyridine (pKa=5.25) was replaced by 3-bromopyridine (pKa=2.84) gave no evidence for any reaction.

EXAMPLE 20

Hydrogen forms of $KCa_2Na_{n-3}Nb_nO_{3n+1}$ with n=4,5,6 and 7 were prepared by treatment of 1 g samples of the potassium compounds in 200 ml of 6M HCl at 60° C. for 16 h. The resulting products were washed with water, dried at room temperature, and heated in air at 100° C. to yield $HCa_2Na_{n-3}Nb_nO_{3n+1}$.

The potassium compounds were prepared as follows: $KCa_2NaNb_4O_{13}$ was prepared by firing in air a stoichiometric mixture of $KCa_2Nb_3O_{10}$ (prepared as described in Example 1) and $NaNbO_3$ at 1000° C. (98 h), 1100° C. (37 h) and finally at 1200° C. (107 h) with several intermediate regrinds, $KCa_2Na_2Nb_5O_{15}$ was prepared by reacting a stoichiometric mixture of $KCa_2NaNb_4O_{13}$ and $NaNbO_3$ in a sealed platinum crucible for 14 h at 1350° C., and a further 62 h at 1350° C., $KCa_2Na_3Nb_6O_{19}$ was prepared by firing a stoichiometric mixture of $KCa_2NaNb_4O_{13}$ and $NaNbO_3$ in a sealed platinum crucible for 63 h at 1350° C., $KCa_2Na_4Nb_7O_{22}$ was prepared similarly by stoichiometric reaction for 275 h at 1350° C. in a sealed platinum crucible with three intermediate regrinds.

Samples of $HCa_2Na_{n-3}Nb_nO_{3n+1}$ (0.5 to 0.1 g) with n=4, 5, 6 and 7 were heated with excess octylamine in heptane (50 ml) for about 100 h. The products were filtered, washed with 95% ethanol and dried at room temperature. X-ray diffraction patterns showed single phase products with no evidence for any unreacted starting material. The tetragonal cell constants are given in Table II together with the value for M=8, n=3 from Table I. The interlayer separation (c axis spacing) increases by about 3.9 Å for each increment in n indicating that the reaction with octylamine changes the interlayer spacing but leaves the structure of each layer unaltered.

EXAMPLE 21

A sample of $HCa_2Na_4Nb_7O_{22}$ (0.435 g) prepared as described in Example 20 was heated in a refluxing solution of octadecylamine in heptane (50 mls) for 88 h. The solid product was filtered, washed with heptane and alcohol and dried at room temperature. An X-ray powder pattern showed the formation of single phase $(H(CH_2)_{18}NH_2)HCa_2Nb_3O_{10}$ material with a c axis spacing of 72 Å.

TABLE II

Lattice Constants for $(C_8H_{17}NH_2)H Ca_2Na_{n-3}Nb_nO_{3n+1}$ Compounds

| n | a (Å) | c (Å) |
|---|---|---|
| 3 | 3.854 | 31.51 |
| 4 | 3.865 | 36.61 |
| 5 | 3.870 | 40.64 |
| 6 | 3.873 | 44.35 |
| 7 | 3.881 | 48.58 |

EXAMPLE 22

A sample of $HCa_2Nb_3O_{10}$ (0.2 g) and 0.6 g of the amine $C_4H_9(OCH_2CH_2)_4OCH_2CHCH_3OCH_2CHCH_3NH_2$ ($RNH_2$) were stirred in 200 mls of water at 60° C. for 72 h. The solid was then filtered from the hot solution, washed with water and dried at room temperature. An X-ray powder pattern of the product showed that the solid had reacted with the amine. The composition as determined by thermogravimetric analysis was found to be $(RHN_2)_{0.5}HCa_2Nb_3O_{10}$.

EXAMPLE 23

A sample of $HCa_2Nb_3O_{10}$ (0.2 g) and 2 g of the amine $CH_3OC_2H_4O(CH_2CHCH_3O)_8CH_2CHCH_3NH_2$ ($RNH_2$) were stirred in 200 mls of water at 60° C. for 18 h. The solid product was filtered hot, washed with water and dried at room temperature. An X-ray powder pattern of the product showed that the solid had reacted with the amine. The composition as determined by thermogravimetric analysis was found to be $(RNH_2)_{0.5}HCa_2Nb_3O_{10}$.

What is claimed is:

1. A composition of matter represented by the formula $$Z_aH_bM_c[A_{n-1}B_nO_{3n+1}]$$

where Z is one or more organic bases having conjugate acids with pKa values greater than about 3; H is hydrogen, M is one or more of K, Rb, Cs, $NH_4$, Li, Na, Tl, and Ag; $0 < a \leq 2$, $c < 1$, and $b+c=1$; A is one or more mono-, di-, and trivalent cations selected from Groups 1a, 2a, and 3b of the Periodic Table of the Elements and the lanthanides; B is one or more transition metals selected from Re, and Groups 4b, 5b, and 6b of the Periodic Table of the Elements; and n is an integer from 3 to 7.

2. The composition of claim 1 wherein $b=1$, and $c=0$.

3. The composition of claim 2 wherein Z is a substituted amine represented by $NR_3$, $NHR_2$, $NH_2R$ where each R is independently selected from the group consisting of $C_1$–$C_{36}$ aliphatic, $C_3$–$C_8$ cycloaliphatic, $C_7$–$C_{24}$ aralkyl, and $C_6$–$C_{10}$ aryl.

4. The composition of claim 3 wherein each R is independently a $C_1$–$C_{36}$ aliphatic group.

5. The composition of claim 3 wherein Z is a substituted amine represented by the formula $NH_2R$ and wherein R is a $C_1$ to $C_{36}$ aliphatic group.

6. The composition of claim 5 wherein R is a $C_1$ to $C_{18}$ n-alkyl group.

7. The composition of claim 1 wherein Z is selected from ethylene diamine, diethylene triamine, and hexamethylene diamine.

8. The composition of claim 5 wherein R is an aliphatic having from about 8–36 carbon atoms interrupted by one or more of ether, ester, or amido linkages.

9. The composition of claim 8 in which Z is a polyether amine.

10. The composition of claim 9 wherein the polyether amine is selected from $$CH_3OC_2H_4O(CH_2\overset{\underset{\displaystyle CH_3}{|}}{C}HO)_8CH_2\overset{\underset{\displaystyle CH_3}{|}}{C}HNH_2,$$

and $$n\text{-}C_4H_9(OCH_2CH_2)_4OCH_2\overset{\underset{\displaystyle CH_3}{|}}{C}HOCH_2\overset{\underset{\displaystyle CH_3}{|}}{C}HNH_2$$

11. The composition of claim 1 wherein A is one or more of Ca and Na, B is Nb, and n is from 3 to 7.

12. The composition of claim 6 wherein A is one or more of Ca and Na, B is Nb, and n is from 3 to 7.

13. The composition of claim 10 wherein A is one or more of Ca and Na, B is Nb, and n is from 3 to 7.

14. A method for preparing layered compositions represented by the formula $$Z_aH_bM_c[A_{n-1}B_nO_{3n+1}]$$

where Z is one or more organic bases having conjugate acids with pKa values greater than about 3, H is hydrogen, M is one or more of K, Rb, Cs, $NH_4$, Li, Na, Tl, and Ag, $0 < a \leq 2$, $C < 1$, and $b+c=1$; A is one or more mono-, di-, and trivalent cations selected from Groups 1a, 2a, and 3b of the Periodic Table of the Elements and the lanthanides; B is one or more transition metals selected from Re, and Groups 4b, 5b and 6b of the Periodic Table of the Elements; and n is an integer from 3 to 7; which method comprises; reacting (i) a solid acid represented by the formula $$H_bM_c[A_{n-1}B_nO_{3n+1}]$$

wherein H, M, A, B, b, c, and n are as defined above, with (ii) one or more organic bases, Z, having conjugate acids with pKa values greater than about 3.

15. The method of claim 14 wherein $b=1$, and $c=0$, for both formulas.

16. The method of claim 15 wherein the organic base, Z, a substituted amine represented by $NR_3$, $NHR_2$, $NH_2R$ where each R is independently selected from the group consisting of $C_1$–$C_{36}$ aliphatic, $C_3$–$C_8$ cycloaliphatic, $C_7$–$C_{24}$ aralkyl, and $C_6$–$C_{10}$ aryl.

* * * * *